(12) United States Patent
Schmidt et al.

(10) Patent No.: US 7,153,974 B2
(45) Date of Patent: Dec. 26, 2006

(54) IONIC LIQUIDS II

(75) Inventors: Michael Schmidt, Seeheim-Jugenheim (DE); Udo Heider, Riedstadt (DE); Winfried Geissler, Rossdorf (DE); Nikolai Ignatyev, Duisburg (DE); Volker Hilarius, Gross-Umstadt (DE)

(73) Assignee: Merck GmbH, Darmstadt (DE)

( * ) Notice: Subject to any disclaimer, the term of this patent is extended or adjusted under 35 U.S.C. 154(b) by 102 days.

(21) Appl. No.: 09/877,259

(22) Filed: Jun. 11, 2001

(65) Prior Publication Data

US 2002/0015884 A1 Feb. 7, 2002

(30) Foreign Application Priority Data

Jun. 9, 2000 (DE) .................... 100 27 995

(51) Int. Cl.
*C07D 233/54* (2006.01)
*H01M 6/04* (2006.01)
*H01M 6/14* (2006.01)
*H01G 9/00* (2006.01)
*H01G 9/035* (2006.01)

(52) U.S. Cl. ............... 548/335.1; 548/343.1; 562/820; 204/242; 252/62.2; 429/328; 429/188

(58) Field of Classification Search ........... 548/343.1, 548/335.1; 562/820; 204/242; 252/62.2; 429/328, 188; 136/263; 361/503
See application file for complete search history.

(56) References Cited

U.S. PATENT DOCUMENTS

| | | |
|---|---|---|
| 5,827,602 A | 10/1998 | Koch et al. |
| 6,210,830 B1 | 4/2001 | Sartori et al. |
| 6,423,454 B1 * | 7/2002 | Heider et al. ............. 429/345 |
| 6,548,212 B1 * | 4/2003 | Heider et al. ............. 429/307 |
| 2002/0015883 A1 * | 2/2002 | Hilarius et al. ........... 429/188 |

* cited by examiner

*Primary Examiner*—Laura L. Stockton
(74) *Attorney, Agent, or Firm*—Miller, White, Zelano, Branigan, P.C.

(57) ABSTRACT

An ionic liquid of the formula $K^+A^-$ wherein $K^+$ and $A^-$ are as defined herein, are suitable for use in electrochemical cells and capacitors. These ionic liquids can also be used in catalysis, as inert solvents, and as hydraulic liquids.

26 Claims, No Drawings

IONIC LIQUIDS II

The invention relates to ionic liquids for use in electrochemical cells and organic syntheses.

Solvent-free ionic liquids or "salts which are molten at room temperature" were described for the first time in U.S. Pat. No. 2,446,331. The problem with these strong Lewis acids is the formation of toxic gases on contact with atmospheric moisture.

Compositions involving AlCl₃ and 1-ethyl-3-methylimidazolium (EMI) chloride have been investigated for a long time. Wilkes and Zaworotko presented novel solvent-free ionic liquids, EMI BF₄ and EMI O₂CCH₃, in 1992 in J. Chem. Soc., Chem. Commun., p. 965. However, these compositions are unsuitable for use as electrolyte in electrochemical cells since the $BF_4^-$ and $CH_3CO_2^-$ anions are oxidised even at relatively low potentials.

DE 196 41 138, incorporated herein by reference, describes a new class of conductive salts, the lithium fluoroalkylphosphates. These salts are distinguished by high electrochemical stability and low tendency towards hydrolysis (M. Schmidt et al. 10$^{th}$ International Meeting on Lithium Batteries, Como 2000). In cycling experiments, these compounds have shown particularly good results and have proven particularly stable.

U.S. Pat. No. 5,827,602, incorporated herein by reference, describes the use of ionic liquids from the group consisting of pyridinium, pyridazinium, pyrimidinium, pyrazinium, imidazoleium, pyrazolium, thiazolium, oxazolium and triazolium salts in electrochemical cells containing imides and methanides as anions. These ionic liquids are particularly suitable for this application owing to good conductivities. The crucial disadvantage consists in the expensive synthesis of the raw materials, in particular the anions.

SUMMARY OF THE INVENTION

An object of the present invention is therefore to provide ionic liquids which have a large liquid range, high thermal stability and low corrosivity and anions which are less expensive to synthesize.

Upon further study of the specification and appended claims, further objects and advantages of this invention will become apparent to those skilled in the art.

These objects are achieved ionic liquids of the general formula $$K^+ A^- \tag{I}$$

in which:
$K^+$ is a cation selected from

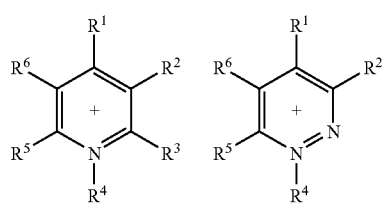

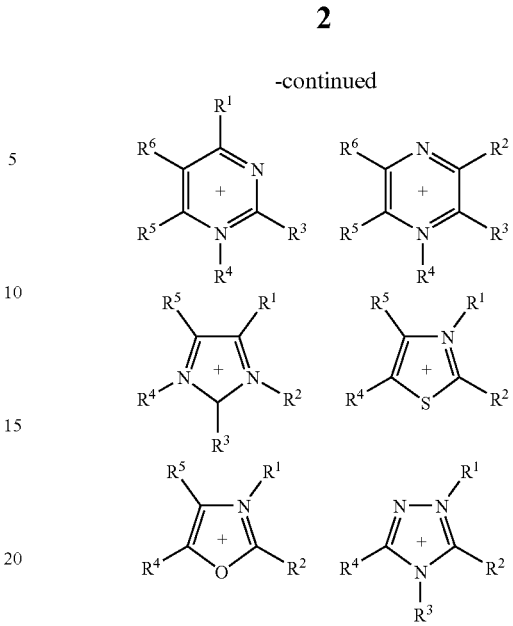

$R^1$ to $R^6$ are identical or different and are each individually
H,
halogen,
an alkyl radical ($C_1$ to $C_8$), which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where 1<n<6 and 0<x≦13,
a phenyl radical which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where 1<n<6 and 0<x≦13, or
one or more pairs of adjacent $R^1$ to $R^6$ can also be an alkylene or alkenylene radical having up to 8 C atoms and which is unsubstituted or partially or fully substituted by further groups, preferably halogen (such as F and Cl), $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where 1<n<6 and 0<x≦13
and
$A^-$ is an anion selected from $$[PF_x(C_yF_{2y+1-z}H_z)_{6-x}]^-$$

where
1≦x<6
1≦y≦8 and
0≦z≦2y+1.

These ionic liquids are suitable as solvents in organic synthesis, but also for use in electrochemical cells. In addition, the ionic liquids are suitable for use in the catalysis of chemical reactions. In addition, they can be used as inert solvents for highly reactive chemicals. A further area is use as hydraulic liquid.

It has been found that the compounds according to the invention are hydrophobic due to the use of perfluorinated alkyl chains, preference being given to relatively long-chain perfluorinated alkyl chains. Furthermore, anhydrous synthesis minimizes undesired introduction of water into the system.

Surprisingly, it has been found that the ionic liquids do not corrode, but instead even passivate the aluminium current collector usually used in electrochemical cells. This enables the cycle stability to be increased. In addition, improved thermal stability of the system through the use of ionic liquids has been observed. It has been found that the addition of solvents of low viscosity enables the conductivity to be improved. Low viscosity together with high conductivity is the prerequisite for use in electrochemical cells. The compounds according to the invention have a large liquid range, making them particularly suitable for these applications.

A prerequisite for use in double layer capacitors is high conductivity. The compounds according to the invention satisfy this criterion and can therefore be employed alone or in mixtures with other solvents or conductive salts. Suitable solvents are those selected from organic carbonates (for example ethylene carbonate, propylene carbonate and derivatives thereof, butylene carbonate, dimethyl carbonate, diethyl carbonate, ethyl methyl carbonate, etc.), organic carboxylic acid esters (for example γ-butyrolactone, methyl formate, methyl acetate, ethyl acetate, ethyl propionate, methyl propionate, methyl butyrate, ethyl butyrate, etc.), organic carboxylic acid amides (for example dimethylformamide, methylformamide, formamide, etc.), organic ethers (for example 1,2-dimethoxyethane, tetrahydrofuran, 2-methyltetrahydrofuran, tetrahydrofuran derivatives, 1,3-dioxolane, dioxane, dioxolane derivatives, etc.) or other aprotic solvents (for example acetonitrile, sulfolane, dimethyl sulfoxide, nitromethane, phosphoric acid triesters, trimethoxymethane, 3-methyl-2-oxazolidinone, etc.). It is likewise possible to use solvent mixtures, such as, for example, ethylene carbonate/dimethyl carbonate (EC/DMC).

In general, electrochemical cells or batteries comprise a cathode, an anode, a separator and an electrolyte. In general, electrochemical capacitors comprise two electrodes, a separator and an electrolyte. See, e.g., FIGS. 3 and 4 of U.S. Pat. No. 5,827,602.

The compounds according to the invention can be used in customary electrolytes with conventional conductive salts. These electrolyte compositions can contain about 1–99 wt % of compounds according to formula (I). Examples of suitable electrolytes are those with conductive salts selected from $LiPF_6$, $LiBF_4$, $LiClO_4$, $LiAsF_6$, $LiCF_3SO_3$, $LiN(CF_3SO_2)_2$ and $LiC(CF_3SO_2)_3$, and mixtures thereof.

The electrolytes may also comprise organic isocyanates (see DE 199 44 603) for reducing the water content.

Complex salts of the following formula (see DE 199 51 804) may also be present in the electrolyte composition $$M^{x+}[EZ]_{x/y}{}^{y-}$$

in which:
x and y are 1, 2 or 3,
$M^{x+}$ is a metal ion,
E is a Lewis acid selected from $BR^1R^2R^3$, $AlR^1R^2R^3$, $PR^1R^2R^3R^4R^5$, $AsR^1R^2R^3R^4R^5$ and $VR^1R^2R^3R^4R^5$
$R^1$ to $R^5$ are identical or different and are in each case individually
a halogen (F, Cl, Br),
an alkyl or alkoxy radical ($C_1$ to $C_8$) which in each case is unsubstituted or partially or fully substituted by F, Cl, or Br,
an aromatic ring selected from phenyl, naphthyl, anthracenyl and phenanthrenyl, which may be bound via oxygen, and which is unsubstituted or monosubstituted to hexasubstituted by alkyl ($C_1$ to $C_8$), F, Cl, or Br,
an aromatic heterocyclic ring selected from pyridyl, pyrazyl and pyrimidyl, which may be bound via oxygen, and which is unsubstituted or monosubstituted to tetrasubstituted by alkyl ($C_1$ to $C_8$), F, Cl, or Br,
or together pairs of $R^1$ to $R^5$ can be an aromatic ring selected from phenylene, naphthylene, anthracenylene and phenanthrenylene, which may be bound via oxygen, and which is unsubstituted or monosubstituted to hexasubstituted by alkyl ($C_1$ to $C_8$), F, Cl, or Br,
an aromatic heterocyclic ring selected from pyridylene, pyrazylene and pyrimidylen, which may be bound via oxygen, and which is unsubstituted or monosubstituted to tetrasubstituted by alkyl ($C_1$ to $C_8$), F, Cl, or Br,
in which the pair of R groups are joined directly to one another by a single or double bond, and
Z is $OR^6$, $NR^6R^7$, $CR^6R^7R^8$, $OSO_2R^6$, $N(SO_2R^6)(SO_2R^7)$, $C(SO_2R^6)(SO_2R^7)(SO_2R^8)$, $OCOR^6$, where
$R^6$ to $R^8$ are each, independently, a hydrogen atom or a group as defined for $R^1$ to $R^5$.

These compounds can be prepared by reacting a corresponding boron or phosphorus Lewis acid/solvent adduct with a lithium or tetraalkylammonium imide, methanide or triflate.

Borate salts (see DE 199 59 722) of the general formula may also be present in the electrolyte composition

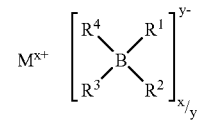

in which:
M is a metal ion, tetraalkylammonium ion, $PR^aR^bR^cR^d$, $P(NR^aR^b)_k R^c{}_m R^d{}_{4-k-m}$ wherein k is 1–4, m is 0–3 and $k+m \leq 4$, $C(NR^aR^b)(NR^{cR}d)(NR^eR^f)$, $C(R^z)_3$, tropylium or a heterocyclic ring containing P, N, S or O, or a fused heterocyclic system containing three rings,
$R^a$ to $R^f$ are each independently H, alkyl having 1 to 8 C atoms or aryl having up to 8 C atoms, in which the aklkyl and aryl groups are unsubtituted or partially substituted by F, Cl, or Br,
$R^z$ is an aromatic or substituted aromatic ring,
x and y are each 1, 2, 3, 4, 5 or 6, and
$R^1$ to $R^4$ are identical or different alkoxy or carboxy radicals ($C_1$–$C_8$) which are optionally bonded directly to one another by a single or double bond.

These borate salts are prepared by reacting lithium tetraalkoxyborate or a 1:1 mixture of lithium alkoxide with a borate with a suitable hydroxyl or carboxyl compound in a ratio of 2:1 or 4:1 in an aprotic solvent.

It is also possible for additives to be present in the electrolyte, such as silane compounds of the following formula (see DE 100 27 626)

$$SiR^1R^2R^3R^4$$

where $R^1$ to $R^4$ are H $C_yF_{2y+1-z}H_z$ $OC_yF_{2y+1-z}H_z$ $OC(O)C_yF_{2y+1-z}H_z$ $OSO_2C_yF_{2y+1-z}H_z$ and
$1 \leq x < 6$
$1 \leq y \leq 8$ and
$0 \leq z \leq 2y+1$ and
R$^1$–R$^4$ can also each be, independently,
an aromatic ring selected from phenyl and naphthyl, which is unsubstituted or monosubstituted or polysubstituted by F, C$_y$F$_{2y+1-z}$H$_z$, OC$_y$F$_{2y+1-z}$H$_z$, OC(O)C$_y$F$_{2y+1-z}$H$_z$, OSO$_2$C$_y$F$_{2y+1-z}$H$_z$ or N(C$_n$F$_{2n+1-z}$H$_z$)$_2$ or
a heterocyclic aromatic ring selected from pyridyl, pyrazyl or pyrimidyl, each of which is unsubstituted or monosubstituted or polysubstituted by F, C$_y$F$_{2y+1-z}$H$_z$, OC$_y$F$_{2y+1-z}$H$_z$, OC(O)C$_y$F$_{2y+1-z}$H$_z$, OSO$_2$C$_y$F$_{2y+1-z}$H$_z$, or N(C$_n$F$_{2n+1-z}$H$_z$)$_2$.

The compounds according to the invention may also be employed in electrolytes comprising lithium fluoroalkylphosphates of the following formula $$\text{Li}^+[\text{PF}_x(\text{C}_y\text{F}_{2y+1-z}\text{H}_z)_{6-x}]^-$$

in which
$1 \leq x \leq 5$
$3 \leq y \leq 8$
$0 \leq z \leq 2y+1$
and the ligands (C$_y$F$_{2y+1-z}$H$_z$) may be identical or different, with the exception of the compounds of the general formula $$\text{Li}^+[\text{PF}_a(\text{CH}_b\text{F}_c(\text{CF}_3)_d)_e]^-$$

in which a is an integer from 2 to 5, b=0 or 1, c=0 or 1, d=2 and e is an integer from 1 to 4, with the provisos that b and c are not simultaneously each =0, and the sum a+e is equal to 6, and the ligands (CH$_b$F$_c$(CF$_3$)$_d$) may be identical or different (see DE 100 089 55).

The process for the preparation of lithium fluoroalkylphosphates is characterised in that at least one compound of the general formula $$\text{H}_m\text{P}(\text{C}_n\text{H}_{2n+1})_{3-m},$$

$$\text{OP}(\text{C}_n\text{H}_{2n+1})_3,$$

$$\text{Cl}_m\text{P}(\text{C}_n\text{H}_{2n+1})_{3-m},$$

$$\text{F}_m\text{P}(\text{C}_n\text{H}_{2n+1})_{3-m},$$

$$\text{Cl}_o\text{P}(\text{C}_n\text{H}_{2n+1})_{5-o},$$

$$\text{F}_o\text{P}(\text{C}_n\text{H}_{2n+1})_{5-o},$$

in each of which
$0 < m < 2$, $1 < n < 8$ and $0 < o < 4$,
is fluorinated by electrolysis in hydrogen fluoride, the resultant mixture of fluorination products is separated by extraction, phase separation and/or distillation, and the resultant fluorinated alkylphosphorane is reacted with lithium fluoride in an aprotic solvent mixture with exclusion of moisture, and the resultant salt is purified and isolated by conventional methods.

The compounds according to the invention can also be employed in electrolytes which comprise salts of the formula $$\text{Li}[\text{P}(\text{OR}^1)_a(\text{OR}^2)_b(\text{OR}^3)_c(\text{OR}^4)_d\text{F}_e]$$

in which $0 < a+b+c+d \leq 5$ and $a+b+c+d+e=6$, and R$^1$ to R$^4$, independently of one another, are alkyl, aryl or heteroaryl radicals, where at least two of R$^1$ to R$^4$ may be bonded directly to one another by a single or double bond (see DE 100 16 801). The compounds are prepared by reacting phosphorus(V) compounds of the general formula $$\text{P}(\text{OR}^1)_a(\text{OR}^2)_b(\text{OR}^3)_c(\text{OR}^4)_d\text{F}_e$$

in which $0 < a+b+c+d \leq 5$ and $a+b+c+d+e=5$, and R$^1$ to R$^4$ are as defined above, with lithium fluoride in the presence of an organic solvent.

It is also possible for the electrolytes to contain ionic liquids of the general formula (see DE 100 265 65)

$$\text{K}^+\text{A}^-$$

in which:
K$^+$ is a cation selected from the group

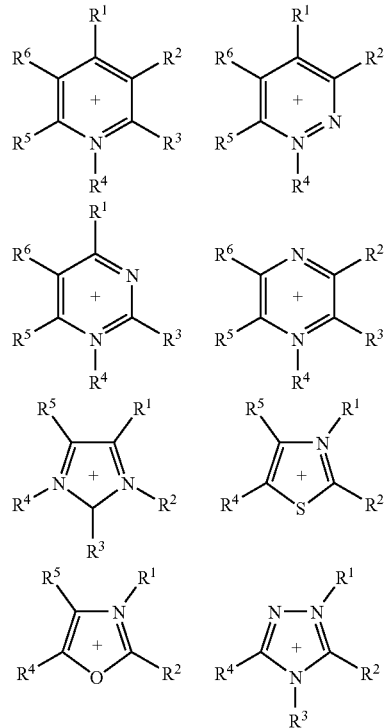

where
R$^1$ to R$^6$ are identical or different and are each individually
H,
halogen,
an alkyl radical (C$_1$ to C$_8$), which is unsubstituted or partially or fully substituted by further groups, preferably F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$) or C$_n$F$_{(2n+1-x)}$H$_x$ where $1 < n < 6$ and $0 < x \leq 13$,
a phenyl radical which is unsubstituted or partially or fully substituted by further groups, preferably F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$) or C$_n$F$_{(2n+1-x)}$H$_x$ where $1 < n < 6$ and $0 < x \leq 13$, or
one or more pairs of adjacent R$^1$ to R$^6$ can also be an alkylene or alkenylene radical having up to 8 C atoms and which is unsubstituted or partially or fully substituted by further groups, preferably halogen (such as F and Cl), N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$) or C$_n$F$_{(2n+1-x)}$H$_x$ where $1 < n < 6$ and $0 < x \leq 13$;

and
A$^-$ is an anion selected from $$[\text{B}(\text{OR}^7)_n(\text{OR}^8)_m(\text{OR}^9)_o(\text{OR}^{10})_p]^-$$

where $0 \leq n, m, o, p \leq 4$, and $m+n+o+p=4$, and $R^7$ to $R^{10}$ are different or identical and are each, individually, an aromatic ring selected from phenyl, naphthyl, anthracenyl and phenanthrenyl, which is unsubstituted or mono-substituted or polysubstituted by $C_nF_{(2n+1-x)}H_x$, where $1<n<6$ and $0<x \leq 13$, or halogen (F, Cl or Br), an aromatic heterocyclic ring selected from pyridyl, pyrazyl and pyrimidyl, which is unsubstituted or monosubstituted or polysubstituted by $C_nF_{(2n+1-x)}H_x$, where $1<n<6$ and $0<x \leq 13$, or halogen (F, Cl or Br), or an alkyl radical ($C_1$ to $C_8$), which is unsubstituted or partially or fully substituted by further groups, preferably F, Cl, , $N(C_nF_{(2n+1-x)}H_x)_2$, $O(C_nF_{(2n+1-x)}H_x)$, $SO_2(C_nF_{(2n+1-x)}H_x)$, or $C_nF_{(2n+1-x)}H_x$, where $1<n<6$ and $0<x \leq 13$; or one or more pairs of $R^7$ to $R^{10}$ can also form an aromatic ring selected from phenylene, naphthylene, anthracenylene and phenanthrenylene, which is unsubstituted or monosubstituted or polysubstituted by $C_nF_{(2n+1-x)}H_x$, where $1<n<6$ and $0<x \leq 13$, or halogen (F, Cl or Br), an aromatic heterocyclic ring selected from pyridylene, pyrazylene and pyrimidylene, which is unsubstituted or monosubstituted or polysubstituted by $C_nF_{(2n+1-x)}H_x$, where $1<n<6$ and $0<x \leq 13$, or halogen (F, Cl or Br), or an alkylene or alkenylene radical having up to 8 C atoms and which is unsubstituted or partially or fully substituted by further groups, preferably halogen (such as F and Cl), $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1<n<6$ and $0<x \leq 13$; or or $OR^7$ to $OR^{10}$, individually or together, are an aromatic (having, e.g., 6 to 14 C atoms) or aliphatic (having, e.g., 1 to 6 C atoms) carboxyl, dicarboxyl, oxysulfonyl or oxycarbonyl radical, which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x \leq 13$.

The compounds according to the invention may also be present in electrolytes comprising compounds of the following formula (see U.S. patent application Ser. No. 60/230,711):

$$NR^1R^2R^3$$

in which $R^1$ and $R^2$ are H, $C_yF_{2y+1-z}H_z$ or $(C_nF_{2n-m}H_m)X$, where X is an aromatic or heterocyclic radical, and $R^3$ is $(C_nF_{2n-m}H_m)Y$, where Y is a heterocyclic radical, or $(C_oF_{2o-p}H_p)Z$, where Z is an aromatic radical, and where n, m, o, p, y and z satisfy the following conditions:

$0 \leq n \leq 6$,
$0 \leq m \leq 2n$,
$2 \leq o \leq 6$,
$0 \leq p \leq 2o$,
$1 \leq y \leq 8$, and
$0 \leq z \leq 2y+1$, for reducing the acid content in aprotic electrolyte systems in electrochemical cells.

It is also possible to employ fluoroalkyl phosphates of the general formula $$M^{n+}[PF_x(C_yF_{2y+1-z}H_z)_{6-x}]_n^-$$

in which
$1 \leq x \leq 6$
$1 \leq y \leq 8$
$0 \leq z \leq 2y+1$
$1 \leq n \leq 3$, and $M^{n+}$ is a monovalent to trivalent cation, in particular:

$NR^1R^2R^3R^4$,
$PR^1R^2R^3R^4$,
$P(NR^1R^2)_kR^3{}_mR^4{}_{4-k-m}$ (where $k=1-4$, $m=0-3$ and $k+m \leq 4$),
$C(NR^1 R^2)(NR^3R^4)(NR^5R^6)$,
$C(aryl)_3$, Rb or tropylium, where $R^1$ to $R^8$ are H, alkyl or aryl ($C_1$–$C_8$), which may be partially substituted by F, Cl or Br, where $M^{n+}=Li^+$, $Na^+$, $Cs^+$, $K^+$ and $Ag^+$ are excluded.

These fluoroalkyl phosphates are obtainable by reacting phosphoranes with a fluoride or metal fluoroalkyl phosphates with a fluoride or chloride in organic aprotic solvents (see DE 100 388 58).

The electrolyte may also comprise a mixture of a) at least one lithium fluoroalkyl phosphate salt of the general formula $$Li^+[PF_x(C_yF_{2y+1-z}H_z)_{6-x}]^-$$

in which
$1 \leq x \leq 5$
$1 \leq y \leq 8$, and
$0 \leq z \leq 2y+1$ and the ligands $(C_yF_{2y+1-z}H_z)$ are in each case identical or different, and b) at least one polymer (see DE 100 58 264).

The electrolyte may also comprise tetrakisfluoroalkyl borate salts of the general formula $$M^{n+}([BR_4]^-)_n$$

in which $M^{n+}$ is a monovalent, divalent or trivalent cation,
the ligands R are in each case identical and are $(C_xF_{2x+1})$, where $1 \leq x \leq 8$, and $n=1$, 2 or 3 (see DE 100 558 11).

The process for the preparation of tetrakisfluoroalkyl borate salts is characterised in that at least one compound of the general formula $M^{n+}([B(CN)_4]^-)_n$, in which $M^{n+}$ and n are as defined above, is fluorinated by reaction with at least one fluorinating agent in at least one solvent, and the resultant fluorinated compound is purified and isolated by conventional methods.

The electrolyte may also comprise borate salts of the general formula $$M^{n+}[BF_x(C_yF_{2y+1-z}H_z)_{4-x}]_n^-$$

in which:

$1<x<3$, $1 \leq y \leq 8$ and $0 \leq z \leq 2y+1$, and

M is a monovalent to trivalent cation ($1 \leq n \leq 3$), apart from potassium and barium, in particular:

Li,
$NR^1R^2R^3R^4$, $PR^5R^6R^7R^8$, $P(NR^5R^6)_kR^7{}_mR^8{}_{4-k-m}$ (where $k-1-4$, $m=0-3$ and $k+m \leq 4$), or
$C(NR^5R^6)(NR^7R^8)(NR^9R^{10})$, where
$R^1$ to $R^4$ are $C_yF_{2y+1-z}H_z$ and
$R^5$ to $R^{10}$ are H or $C_yF_{2y+1-z}H_z$, or\
an aromatic heterocyclic cation, in particular a nitrogen- and/or oxygen- and/or sulfur-containing aromatic heterocyclic cation (see DE 101 031 89). The process for the preparation of these compounds is characterised in that a) $BF_3$/solvent complexes are reacted 1:1 with alkyllithium with cooling, the majority of the solvent is removed after slow warming, and the solid is subsequently filtered off and washed with a suitable solvent, or b) lithium salts in a suitable solvent are reacted 1:1 with B(CF$_3$)F$_3$ salts, the mixture is stirred at elevated temperature, the solvent is removed, aprotic non-aqueous solvents, preferably solvents which are used in electrochemical cells, are added to the reaction mixture, and the mixture is dried, or c) B(CF$_3$)F$_3$ salts are reacted 1:1 to 1:1.5 with lithium salts in water at elevated temperature and heated at the boiling point for from 0.5 to 2 hours, the water is removed, aprotic non-aqueous solvents, preferably solvents which are used in electrochemical cells, are added to the reaction mixture and the mixture is dried.

The electrolyte may also comprise fluoroalkyl phosphate salts of the general formula $$M^{n+}([PF_x(C_yF_{2y+1-z}H_z)_{6-x}]^-)_n$$

in which
M$^{n+}$ is a monovalent, divalent or trivalent cation,
$1 \leq x \leq 5$,
$1 \leq y \leq 8$ and
$0 \leq z \leq 2y+1$, n=1, 2 or 3, and the ligands (C$_y$F$_{2y+1-z}$H$_z$) are in each case identical or different, where the fluoroalkyl phosphate salts in which M$^{n+}$ is a lithium cation and the salts
M$^+$([PF$_4$(CF$_3$)$_2$]$^-$) where M$^+$=Cs$^+$, Ag$^+$ or K$^+$,
M$^+$([PF$_4$(C$_2$F$_5$)$_2$]$^-$) where M$^+$=Cs$^+$,
M$^+$([PF$_3$(C$_2$F$_5$)$_3$]$^-$) where M$^+$=Cs$^+$, K$^+$, Na$^+$ or para-Cl (C$_6$H$_4$)N$_2^+$,
M$^+$([PF$_3$(C$_3$F$_7$)$_3$]$^-$) where M$^+$=Cs$^+$, K$^+$, Na$^+$, para-Cl(C$_6$H$_4$) N$_2^+$ or para-O$_2$N(C$_6$H$_4$)N$_2^+$ are excluded (see DE 100 558 12).

The process for the preparation of these fluoroalkyl phosphate salts is characterised in that at least one compound of the general formula $$H_rP(C_sH_{2s+1})_{3-r},$$

$$OP(C_sH_{2s+1})_3,$$

$$Cl_rP(C_sH_{2s+1})_{3-r},$$

$$F_rP(C_sH_{2s+1})_{3-r},$$

$$Cl_rP(C_sH_{2s+1})_{5-t} \text{ and/or}$$

$$F_rP(C_sH_{2s+1})_{5-t},$$

in which in each case
$0 \leq r \leq 2$
$3 \leq s \leq 8$ and
$0 \leq t \leq 4$, is fluorinated by electrolysis in hydrogen fluoride, the resultant mixture of fluorination products is separated, and the resultant fluorinated alkylphosphorane is reacted with a compound of the general formula M$^{n+}$(F$^-$)$_n$, in which M$^{n+}$ and n are as defined above, in an aprotic solvent or solvent mixture with exclusion of moisture, and the resultant fluoroalkyl phosphate salt is purified and isolated by conventional methods.

The compounds according to the invention may be present in electrolytes which comprise fluoroalkyl phosphate salts (see DE 101 09 032) of the formula $$(M^{a+})_b[(C_nF_{2n+1-m}H_m)_yPF_{5-y}(CR_1R_2)_xPF_{5-y}(C_nF_{2n+1-m}H_m)_y]^{(2-)}_{(a*b/2)}$$

in which
M$^{a+}$ is a monovalent, divalent or trivalent cation,
a=1, 2 or 3, b=2 for a=1, b=2 for a=3, b=1 for a=2 and in each case
$1 \leq n \leq 8$,
$0 \leq m \leq 2$ for n=1 or 2,
$0 \leq m \leq 4$ for $3 \leq n \leq 8$,
$1 \leq x \leq 12$,
$0 \leq y \leq 2$,
where R$_1$ and R$_2$ are in each case identical or different and are selected from the group consisting of fluorine, hydrogen, alkyl, fluoroalkyl and perfluoroalkyl substituents, and
where in each case the substituents (C$_n$F$_{2n+1-m}$H$_m$) are identical or different. These compounds are prepared by reacting at least one fluoro-α,ω-bis(alkylfluorophosphorano)alkane with at least one fluoride salt of the general formula (M$^{a+}$) [F$^-$]$_a$, in which (M$^{a+}$) and a are as defined above, in solution to give a fluoroalkyl phosphate salt, and, if desired, purifying and/or isolating the latter by conventional methods.

The compounds according to the invention can be used in electrolytes for electrochemical cells containing positive-electrode material consisting of coated metal cores selected from the group consisting of Sb, Bi, Cd, In, Pb, Ga and tin or alloys thereof (see DE 100 16 024). The process for the preparation of this positive-electrode material is characterised in that a) a suspension or sol of the metal or alloy core in urotropin is prepared,
b) the suspension is emulsified with C$_5$–C$_{12}$-hydrocarbons,
c) the emulsion is precipitated onto the metal or alloy cores, and
d) the metal hydroxides or oxyhydroxides are converted into the corresponding oxide by heating the system.

The compounds according to the invention can also be employed in electrolytes for electrochemical cells having negative electrodes made from customary lithium intercalation and insertion compounds, but also having negative-electrode materials made of lithium mixed oxide particles coated with one or more metal oxides (DE 199 22 522). They can also be made of lithium mixed oxide particles coated with one or more polymers (DE 199 46 066). The compounds according to the invention can likewise be employed in systems having negative electrodes made of lithium mixed oxide particles having one or more coatings of alkali metal compounds and metal oxides (DE 100 14 884). The process for the preparation of these materials is characterised in that the particles are suspended in an organic solvent, an alkali metal salt compound suspended in an organic solvent is added, metal oxides dissolved in an organic solvent are added, a hydrolysis solution is added to the suspension, and the coated particles are subsequently filtered off, dried and calcined. The compounds according to the invention can likewise be employed in systems comprising positive-electrode materials with doped tin oxide (DE 100 257 61). This positive-electrode material is prepared by a) adding urea to a tin chloride solution,
b) adding urotropin and a suitable doping compound to the solution,
c) emulsifying the resultant sol in petroleum ether,
d) washing the resultant gel and removing the solvent by suction, and
e) drying and heating the gel.

The compounds according to the invention can likewise be employed in systems comprising positive-electrode materials with reduced tin oxide (see DE 100 257 62). This positive-electrode material can be prepared by a) adding urea to a tin chloride solution,
b) adding urotropin to the solution, c) emulsifying the resultant sol in petroleum ether,
d) washing the resultant gel and removing the solvent by suction,
e) drying and heating the gel, and
f) exposing the resultant $SnO_2$ to a reducing gas stream in an aeratable oven.

A general example of the invention is explained in greater detail below.

An anion selected from the formula

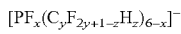

$[PF_x(C_yF_{2y+1-z}H_z)_{6-x}]^-$ where $1 \leq x < 6$ $1 \leq y \leq 8$ and $0 \leq z \leq 2y+1$ is prepared using a known process from DE 196 411 38.

A cation selected from the following formulas

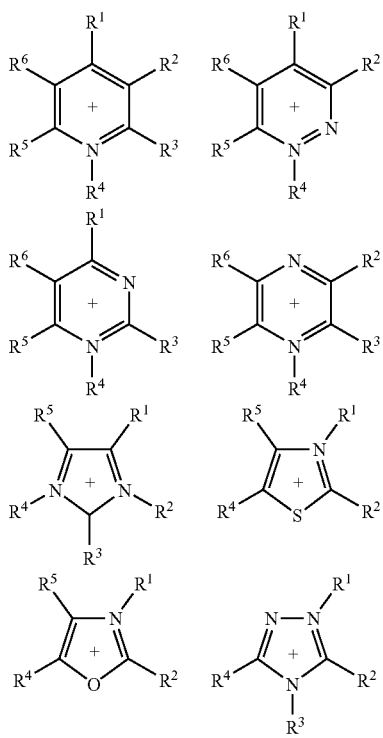

is prepared using a known process from U.S. Pat. No. 5,827,602. The starting materials are reacted in an aprotic organic solvent at temperatures in the liquid range of the solvent for from about 0.5 to 12 hours, preferably for 1–4 hours.

In order to remove the by-products, the mixture is cooled to −30° C., for example to from −10° C. to −20° C. in the case of LiCl as by-product, and the precipitating by-product is filtered off, preferably filtered off by vacuum.

The solvent/product mixture can be employed directly in the electrolyte. If desired, the solvent can also be distilled off and the resultant product dried in order to be employed in the stated applications.

The following examples are intended to explain the invention in greater detail, but without restricting it.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 100 27 995.3, filed Jun. 9, 2000, is hereby incorporated by reference.

EXAMPLES

Example 1

Synthesis of 1-ethyl-3-methylimidazolium tris(pentafluoroethyl)trifluorophosphate Lithium tris(pentafluoroethyl)trifluorophosphate is synthesized in accordance with DE 196 411 38. The product is reacted in acetonitrile in accordance with the following reaction equation:

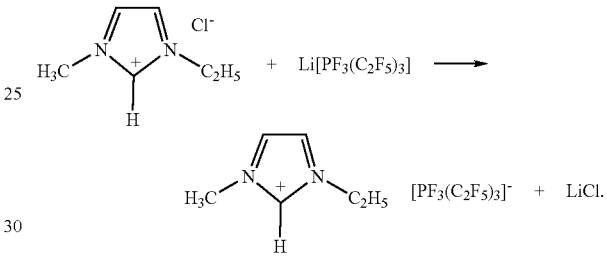

The reaction mixture is vacuum filtered through a glass frit with cooling in order to remove the LiCl formed as by-product. The solvent is distilled off under reduced pressure, and the resultant 1-ethyl-3-methylimidazolium tris(pentafluoroethyl)trifluorophosphate is dried under reduced pressure.

Example 2

Synthesis of 1,2-dimethyl-3-propylimidazolium tris(pentafluoroethyl)trifluorophosphate Lithium tris(pentafluoroethyl)trifluorophosphate is synthesized in accordance with DE 196 411 38. The product is reacted in acetonitrile in accordance with the following reaction equation:

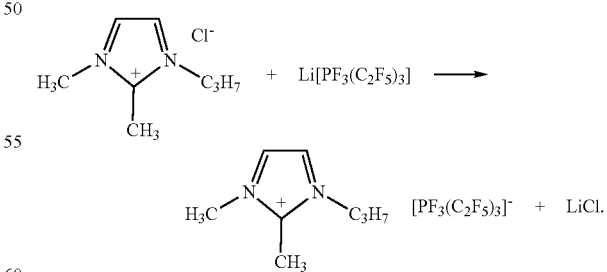

The reaction mixture is vacuum filtered through a glass frit with cooling in order to remove the LiCl formed as by-product. The solvent is distilled off under reduced pressure, and the resultant 1,2-dimethyl-3-propylimidazolium tris(pentafluoroethyl)trifluorophosphate is dried under reduced pressure.

Example 3

Synthesis of 1-ethyl-3-methylimidazolium tris(nonafluorobutyl)trifluorophosphate Lithium tris(nonafluorobutyl)trifluorophosphate is synthesized analogously to lithium tris(pentafluoroethyl)trifluorophosphate. The product is reacted in acetonitrile in accordance with the following reaction equation:

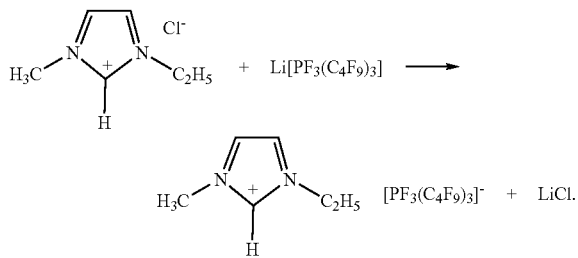

The reaction mixture is vacuum filtered through a glass frit with cooling in order to remove the LiCl formed as by-product. The solvent is distilled off under reduced pressure, and the resultant 1-ethyl-3-methylimidazolium tris(nonafluorobutyl)trifluorophosphate is dried under reduced pressure.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula $$K^+A^- \quad (I)$$

wherein:

$K^+$ is a cation selected from

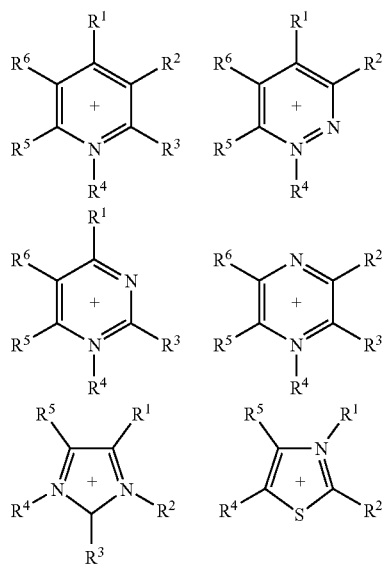

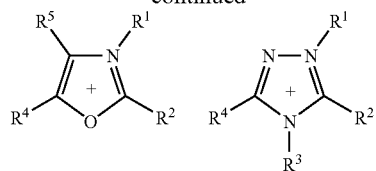

where $R^1$ to $R^6$ are identical or different and are each individually
H,
halogen,
an alkyl radical ($C_1$ to $C_8$), which is unsubstituted or partially or fully substituted by F, Cl, $N(C_nF_{(2n+1-x)}H_x)_2$, $O(C_nF_{(2n+1-x)}H_x)$, or $(C_nF_{(2n+1-x)}H_x)$, where $1<n<6$ and $0<x\leq13$,
a phenyl radical which is unsubstituted or partially or fully substituted by F, Cl, $N(C_nF_{(2n+1+x)}H_x)_2$, $O(C_nF_{(2n+1-1)}H_x)$, $SO_2(C_nF_{(2n+1-x)}H_x)$ or $C_nF_{(2n+1-x)}H_x$ where $1<n<6$ and $0<x\leq13$, or
one or more pairs of adjacent $R^1$ to $R^6$ can also be an alkylene or alkenylene radical having up to 8 C atoms and which is unsubstituted or partially or fully unsubstituted by halogen, $N(C_nF_{(2n+1x)}H_x)_2$, $O(C_nF_{(2n+1-x)}H_x)$, $SO_2(C_nF_{(2n+1-x)}H_x$ or $C_nF_{(2n+1-x)}H_x$ where $1<n<6$ and $0\leq x\leq13$; and $A^-$ is an anion of the following formula $$[PF_x(C_yF_{2y+1-z}H_z)_{6-x}]^-$$

where
$1 \leq x < 6$
$2 \leq y \leq 8$ and
$0 \leq z \leq 2y+1$.

2. A compound according to claim 1, wherein at least one $R^1$ to $R^6$ group is a halogen.

3. A compound according to claim 1, wherein at least one $R^1$ to $R^6$ group is an alkyl radical ($C_1$ to $C_8$), which is unsubstituted or partially or fully substituted by F, Cl, $N(C_nF_{(2n+1-x)}H_x)_2$, $O(C_nF_{(2n+1-x)}H_x)$, or $(C_nF_{(2n+1-x)}H_x)$, where $1<n<6$ and $0<x\leq13$.

4. A compound according to claim 1, wherein at least one $R^1$ to $R^6$ group is a phenyl radical which is unsubstituted or partially or fully substituted by F, Cl, $N(C_nF_{(2n+1-x)}H_x)_2$, $O(C_nF_{(2n+1-1)}H_x)$, $SO_2(C_nF_{(2n+1-x)}H_x)$ or $C_nF_{(2n+1-x)}H_x$ where $1<n<6$ and $0<x\leq13$.

5. A compound according to claim 1, wherein at least one adjacent pair of $R^1$ to $R^6$ is an alkylene or alkenylene radical having up to 8 C atoms and which is unsubstituted or partially or fully unsubstituted by halogen, $N(C_nF_{(2n+1x)}H_x)_2$, $O(C_nF_{(2n+1-x)}H_x)$, $SO_2(C_nF_{(2n+1-x)}H_x$ or $C_nF_{(2n+1-x)}H_x$ where $1<n<6$ and $0\leq x\leq13$.

6. A compound according to claim 1, wherein said compound has at least one perfluorinated alkyl group.

7. A compound according to claim 1, wherein said compound contains at least one $C_yF_{2y+1-z}H_z$ group selected from $C_2F_5$ and $C_4F_9$.

8. An electrochemical cell comprising a cathode, an anode, a separator, and an ionic liquid of claim 1.

9. A capacitor comprising of at least a pair of electrodes, a separator, and an ionic liquid of claim 1.

10. An electrolyte composition comprising an ionic liquid of claim 1 and an aprotic solvent.

11. An electrolyte composition comprising an ionic liquid of claim 1 and a conductive salt.

12. A compound according to claim 1, wherein said compound is: 1-ethyl-3-methylimidazolium tris(pentafluoroethyl)trifluorophosphate; 1,2-dimethyl-3-propylimidazolium tris(pentafluoroethyl)trifluorophosphate; or 1-ethyl-3-methylimidazolium tris(nonafluorobutyl)trifluorophosphate.

13. A compound according to claim 12, wherein said compound is 1-ethyl-3-methylimidazolium tris(pentafluoroethyl)trifluorophosphate.

14. A compound according to claim 1, wherein $R^1$ to $R^6$ are each H or a $C_1$ to $C_8$ alkyl, which is unsubstituted or partially or fully substituted by F, Cl, $N(C_nF_{(2n+1-x)}H_x)_2$, $O(C_nF_{(2n+1-x)}H_x)$, or $(C_nF_{(2n+1-x)}H_x)$ where $1<n<6$ and $0<x\leq13$.

15. A compound according to claim 1, wherein $R^1$ to $R^6$ are each H or a $C_1$ to $C_8$ alkyl.

16. An electrolyte composition according to claim 11, wherein said conductive salt is $LiPF_6$, $LiBF_4$, $LiClO_4$, $LiAsF_6$, $LiCF_3SO_3$, $LiN(CF_3SO_2)_2$, $LiC(CF_3SO_2)_3$ or mixture thereof.

17. An electrolyte composition according to claim 11, wherein said composition contains 1–99 wt% of said ionic liquid.

18. An electrolyte composition according to claim 11, wherein said composition further contains an organic isocyanate.

19. A compound according to claim 1, wherein $1\leq z \leq 2y+1$.

20. A compound of the formula $$K^+A^- \quad (I)$$

wherein:

$K^+$ is a cation selected from

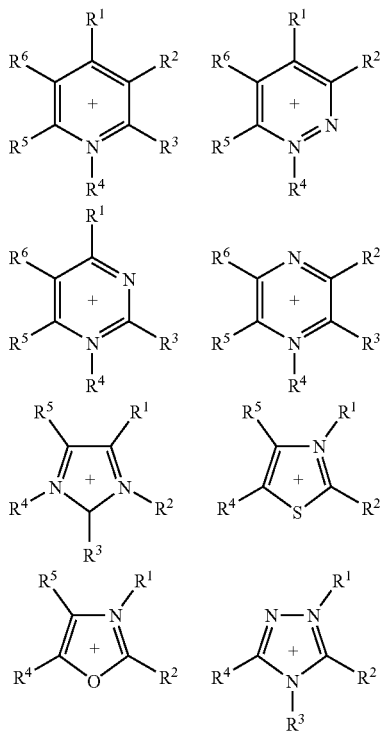

where $R^1$ to $R^6$ are identical or different and are each individually
H,
halogen,
an alkyl radical ($C_1$ to $C_8$), which is unsubstituted or partially or fully substituted by F, Cl, $N(C_nF_{(2n+1-x)}H_x)_2$, $O(C_nF_{(2n+1-x)}H_x)$, or $(C_nF_{(2n+1-x)}H_x)$, where $1<n<6$ and $0<x\leq13$, a phenyl radical which is unsubstituted or partially or fully substituted by F, Cl, $N(C_nF_{(2n+1+x)}H_x)_2$, $O(C_nF_{(2n+1-1)}H_x)$, $SO_2(C_nF_{(2n+1-x)}H_x)$ or $C_nF_{(2n+1-x)}H_x$ where $1<n<6$ and $0<x\leq13$, or one or more pairs of adjacent $R^1$ to $R^6$ can also be an alkylene or alkenylene radical having up to 8 C atoms and which is unsubstituted or partially or fully unsubstituted by halogen, $N(C_nF_{(2n+1x)}H_x)_2$, $O(C_nF_{(2n+1-x)}H_x)$, $SO_2(C_nF_{(2n+1-x)}H_x$ where $1<n<6$ and $0\leq x\leq 13$; and $A^-$ is an anion of the following formula $$[PF_x(C_yF_{2y+1-z}H_z)_{6-x}]^-$$

where $1\leq x<6$ $2\leq y\leq 8$ and $1\leq z\leq 2y1$.

21. A compound according to claim 1, wherein $K^+$ is

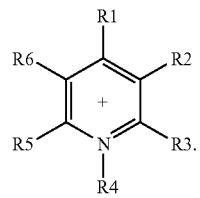

22. A compound according to claim 1, wherein $K^+$ is

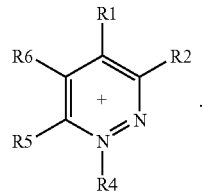

23. A compound according to claim 1, wherein $K^+$ is

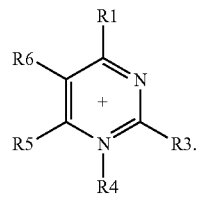

24. A compound according to claim 1, wherein $K^+$ is

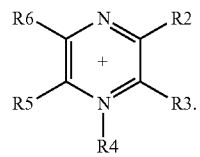

25. A compound according to claim 1, wherein K⁺ is
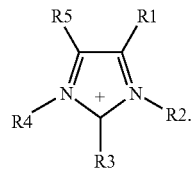
26. A compound according to claim 1, wherein K⁺ is
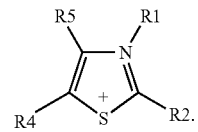
* * * * *

UNITED STATES PATENT AND TRADEMARK OFFICE
CERTIFICATE OF CORRECTION

PATENT NO. : 7,153,974 B2
APPLICATION NO. : 09/877259
DATED : December 26, 2006
INVENTOR(S) : Schmidt et al.

It is certified that error appears in the above-identified patent and that said Letters Patent is hereby corrected as shown below:

Column 14, line 20, reads "$N(C_nF_{(2n+1+x)}H_x)_2$," should read --$N(C_nF_{(2n+1-x)}H_x)_2$,--
Column 14, line 21, reads "$F_{(2n+1-1)}H_x)$," should read --$F_{(2n+1-x)}H_x)$,--
Column 14, line 26, reads "$N(C_nF_{(2n+1x)}H_x)_2$," should read --$N(C_nF_{(2n+1-x)}H_x)_2$,--
Column 14, line 46, reads "$O(C_nF_{(2n+1-1)}H_x)_2$," should read --$O(C_nF_{(2n+1-x)}H_x)_2$,--
Column 14, line 51-52, reads "$N(C_nF_{(2n+1x)}H_x)_2$," should read --$N(C_nF_{(2n+1-x)}H_x)_2$,--
Column 14, line 62, reads "comprising of at" should read --comprising at--
Column 15, line 18-19, reads "or mixture" should read --or a mixture--
Column 16, line 6, reads "$N(C_nF_{(2n+1+x)}H_x)_2$," should read --$N(C_nF_{(2n+1-x)}H_x)_2$,--
Column 16, line 7, reads "$F_{(2n+1-1)}H_x)$," should read --$F_{(2n+1-x)}H_x)$,--
Column 16, line 12, reads "$N(C_nF_{(2n+1x)}H_x)_2$," should read --$N(C_nF_{(2n+1-x)}H_x)_2$,--
Column 16, line 13, reads "$SO_2(C_nF_{(2n+1+x)}H_x$ where" should read --$SO_2(C_nF_{(2n+1-x)}H_x)$ or $C_nF_{(2n+1-x)}H_x$ where--
Column 16, line 21, reads "$1 \leq z \leq 2y1$." should read --$1 \leq z \leq 2y+1$.--

Signed and Sealed this

Second Day of December, 2008

JON W. DUDAS
*Director of the United States Patent and Trademark Office*